United States Patent [19]

Maruta et al.

[11] Patent Number: 4,990,689

[45] Date of Patent: Feb. 5, 1991

[54] 2,4-BIS(2-HYDROXYHEXAFLUORO-2-PROPYL)FLUOROBENZENE AND METHOD OF PREPARING SAME

[75] Inventors: Masamichi Maruta; Takayuki Nishimiya, both of Kawagoe City, Japan

[73] Assignee: Central Glass Company, Limited, Ube City, Japan

[21] Appl. No.: 368,585

[22] Filed: Jun. 20, 1989

[30] Foreign Application Priority Data

Jun. 23, 1988 [JP] Japan .................................. 63-155717

[51] Int. Cl.$^5$ ........................ C07C 33/46; C07C 33/24
[52] U.S. Cl. .................................... 568/812; 568/811
[58] Field of Search .............................. 568/811, 812

[56] References Cited

U.S. PATENT DOCUMENTS 3,236,894  2/1966  England ............................... 568/812
4,873,375  10/1989  Kubo et al. .......................... 568/812

OTHER PUBLICATIONS

"Perhalo Ketones. v.[1] The Reaction of Perhaloacetones with Aromatic Hydrocarbons", by Basil S. Farah, et al., J. Org. Chem., 30, pp. 998–1001, 1965.

*Primary Examiner*—Werren B. Lone
*Attorney, Agent, or Firm*—Fleit, Jacobson, Cohn, Price, Holman & Stern

[57] ABSTRACT

By reacting fluorobenzene with hexafluoroacetone in the pressure of a Lewis acid catalyst, e.g. aluminum chloride, a novel compound 2,4-bis(2-hydroxyhexafluoro-2-propyl)fluorobenzene is formed at high yield with little formation of isomers. The novel compound is useful as a cross-linking agent for some polymers and also as a material of some polymers.

4 Claims, No Drawings

4,990,689

2,4-BIS(2-HYDROXYHEXAFLUORO-2-PROPYL)-FLUOROBENZENE AND METHOD OF PREPARING SAME

BACKGROUND OF THE INVENTION

This invention relates to a novel compound, viz. 2,4-bis(2-hydroxyhexafluoro-2-propyl)fluorobenzene, which is useful as a cross-linking agent for some polymers and also as a material of some polymers.

It is known that 1,3- and 1,4-bis(2-hydroxyhexafluoro-2-propyl)benzenes are obtained by reaction between hexafluoroacetone and benzene in the presence of aluminum chloride. (J. Org. Chem., 30, 998(1965)) This reaction gives a mixture of the 1,3- and 1,4-isomers, whereby a separating process is needed for isolation of either of the isomers.

As far as we know, no literature shows fluorine substitution of the benzene nucleus of bis(2-hydroxyhexafluoro-2-propyl)benzene.

SUMMARY OF THE INVENTION

It is an object of the present invention to provide a novel derivative of bis(2-hydroxyhexafluoro-2-propyl)benzene and a method of easily preparing the novel compound at high yield.

The present invention provides 2,4-bis(2-hydroxyhexafluoro-2-propyl)fluorobenzene as a novel compound which is useful as a cross-linking agent for some polymers and also as a material of polyethers and some other polymers.

For preparing the novel compound, the invention provides a method comprising reacting fluorobenzene with hexafluoroacetone in the presence of a Lewis acid as catalyst.

The reaction in this method proceeds under mild conditions and forms 2,4-bis(2-hydroxyhexafluoro-2-propyl)fluorobenzene with very high selectivity, i.e. with little formation of unwanted isomers.

DETAILED DESCRIPTION OF THE INVENTION

In the method according to the invention preferred examples of the Lewis acid catalyst are aluminum chloride, aluminum bromide and boron trifluoride.

The reaction between fluorobenzene and hexafluoroacetone can be carried out by direct contact of the reactants with each other without using any medium, but if desired the reaction may be carried out in a solvent which does not react with the reactants or the catalyst. In the latter case it is suitable to select the solvent from ethers, carbon disulfide and methylene chloride.

The reaction according to the invention is carried out by first charging a reactor with fluorobenzene and a Lewis acid catalyst and, if desired, a solvent for aiding dispersion of the reactants and catalyst or for any other purpose, and then introducing hexafluoroacetone into the reactor while stirring fluorobenzene. Since hexafluoroacetone is a gas under normal temperature and normal pressure, the apparatus for the reaction includes a gas feed system to introduce this reactant into the reactor at a variable rate from a gas container such as a bomb.

It is practicable to carry out the reaction under normal pressure, and it is an option to carry out the reaction in an autoclave under pressure of about 2-7 atm for the purpose of enhancing the rate of reaction. When the reaction is carried out under normal pressure, it is necessary to reflux the reaction gas with sufficient cooling by using, for example, a condenser cooled with dry ice. Preferably the reaction is carried out at temperatures not higher than 30° C.

Of course it is necessary to introduce at least 2 mols of hexafluorobenzene into the reactor per mol of fluorobenzene, but it is not necessary to use a large excess of hexafluoroacetone. The reaction is completed in a few hours to tens of hours.

EXAMPLE 1

A three-necked flask having a capacity of 1 liter was equipped with a gas introducing pipe, theremometer, magnetic stirring bars and a reflux condenser cooled with dry ice bath. The flask was charged with 96 g (1 mol) of fluorobenzene and 70 g of anhydrous aluminum chloride. The flask was kept cooled in ice bath, and hexafluoroacetone was introduced into the flask at a controlled rate such that the reaction temperature did not exceed 30° C. This operation was continued until the feed of 166 g (1 mol) of hexafluoroacetone into the flask. After that the ice bath was removed, and 409 g (2.46 mols) of hexafluoroacetone was further introduced into the flask while controlling the rate of introduction so as not to cause vigorous reflux of the introduced hexafluoroacetone. It took 30 hr (net operation time) to introduce 409 g of hexafluoroacetone to thereby complete the intended reaction.

After the above operations the reaction liquid was poured into 500 ml of water, and, after removing aluminum chloride, an organic layer separated as a bottom layer was recovered. The organic product was dried with anhydrous magnesium sulfate and then distilled to obtain 312 g of 2,4-bis-(2-hydroxhexafluoro-2-propyl)-fluorobenzene (99.9% purity and 73% yield) as a distillate at 88°-92° C./12 mmHg. Analysis gave the following results.

$^1$H-NMR (CDCl$_3$): $\delta$3.60 ppm (s, 1H, OH), $\delta$4.02 ppm (d, J=6.5 Hz, 1H, OH), $\delta$7.26 ppm (d of d, J=11.6 Hz, 8.9 Hz, 1H, Ar), $\delta$7.76–7.98 ppm (m, 1H, Ar), $\delta$8.23 ppm (d of d, J=7.14 Hz, 1.8 Hz, 1H, Ar).

$^{19}$F-NMR (CDCl$_3$): $\delta$75.4 ppm (s, 3F), $\delta$75.6 ppm (s, 3F), $\delta$76.1 ppm (s, 6F), $\delta$108.6 ppm (m, 1F).

Mass Spectrometry: 428 (M+).

EXAMPLE 2

A 1-liter autoclave was charged with 192 g (2 mols) of fluorobenzene and 80 g of anhydrous aluminum chloride and kept cooled in ice bath. Then 708 g (4.26 mols) of hexafluoroacetone was introduced into the autoclave at such a rate that the temperature in the autoclve did not exceed 30° C. It took 8 hr to introduce the entire quantity of hexafluoroacetone. After that stirring of the reaction system was continued for 16 hr to thereby complete the intended reaction.

After the above operations the residual gas was purged from the autoclave, and the reaction liquid was poured into 500 ml of water to recover an oily product separated as a bottom layer. The remaining liquid was subjected to extraction with methylene chloride, and the extract was added to the first recovered oily product. Without drying, the product was distilled to obtain 761 g of 2,4-bis(2-hydroxyhexafluoro-2-propyl)fluorobenzene (99.9% purity and 88.4% yield) as a distillate at 97°-98° C./16 mmHg. The freezing point of the obtained compound was measured to be 19.5°-20.0° C.

What is claimed is:

1. 2,4-bis(2-hydroxyhexafluoro-2-propyl)fluorobenzene.

2. A method of preparing 2,4-bis(2-hydroxyhexafluoro-2-propyl)fluorobenzene, comprising reacting fluorobenzene with hexafluoroacetone in the presence of a Lewis acid as catalyst, wherein the reaction is carried out at a temperature not higher than 30° C. and a pressure not lower than atmospheric pressure.

3. A method according to claim 2, wherein said Lewis acid is selected from the group consisting of aluminum chloride, aluminum bromide and boron trifluoride.

4. A method according to claim 2, wherein the reaction is carried out in an organic liquid medium.

* * * * *